(12) United States Patent
Suzuki et al.

(10) Patent No.: US 8,614,361 B2
(45) Date of Patent: Dec. 24, 2013

(54) PROCESS FOR PREPARATION OF 2,3,3,3-TETRAFLUOROPROPENE

(75) Inventors: Atsushi Suzuki, Settsu (JP); Masatoshi Nose, Settsu (JP); Tsuneo Yamashita, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 13/265,396

(22) PCT Filed: Apr. 22, 2010

(86) PCT No.: PCT/JP2010/057727
§ 371 (c)(1),
(2), (4) Date: Oct. 20, 2011

(87) PCT Pub. No.: WO2010/123154
PCT Pub. Date: Oct. 28, 2010

(65) Prior Publication Data
US 2012/0041239 A1 Feb. 16, 2012

Related U.S. Application Data

(60) Provisional application No. 61/202,967, filed on Apr. 23, 2009.

(51) Int. Cl.
*C07C 17/00* (2006.01)

(52) U.S. Cl.
USPC .......................... 570/156; 570/165

(58) Field of Classification Search
USPC ................ 570/156, 165
See application file for complete search history.

(56) References Cited

U.S. PATENT DOCUMENTS

| | | | |
|---|---|---|---|
| 2,931,840 A | 4/1960 | Marquis | |
| 3,996,299 A | 12/1976 | Fozzard | |
| 6,337,299 B1 | 1/2002 | Shibanuma et al. | |
| 6,433,233 B1 | 8/2002 | Kanemura et al. | |
| 2006/0258891 A1 | 11/2006 | Mukhopadhyay et al. | |
| 2007/0197842 A1 | 8/2007 | Mukhopadhyay et al. | |
| 2008/0058562 A1 | 3/2008 | Petrov et al. | |
| 2009/0240090 A1* | 9/2009 | Merkel et al. | 570/160 |

FOREIGN PATENT DOCUMENTS

| | | |
|---|---|---|
| JP | 63-211245 | 9/1988 |
| JP | 5-146680 | 6/1993 |
| JP | 11-171806 | 6/1999 |
| WO | 2009/003084 | 12/2008 |
| WO | 2010/013796 | 2/2010 |
| WO | 2010/016401 | 2/2010 |

OTHER PUBLICATIONS

International Search Report issued Jan. 20, 2011 in International (PCT) Application No. PCT/JP2010/057727 and Written Opinion.
R. N. Haszeldine et al., "Free-Radical Additions to Unsaturated Systems. Part XVII. Reaction of Trifluoroiodomethane with Mixtures of Ethylene and Vinyl Fluoride and of Ethylene and Propene", Journal of Chemical Society, vol. 3, pp. 414-421, Jan. 1, 1970.
R. N. Haszeldine et al., "Addition of Free Radicals to Unsaturated Systems. Part XIII. Direction of Radical Addition to Chloro-1: 1-difluoroethylene", J. Chem. Soc., pp. 2193-2197, 1957.
R. E. Banks et al., "Preparation of 2,3,3,3-tetrafluoropropene from Trifluoroacetylacetone and Sulphur Tetrafluoride", Journal of Fluorine Chemistry, vol. 82, pp. 171-174, 1997.
Manufacturing technology research of 2,3,3,3-tetrafluoropropene (HFC-1234y1), Organofluorine Industry, 2008, No. 4, pp. 38-41.

* cited by examiner

*Primary Examiner* — Jafar Parsa
(74) *Attorney, Agent, or Firm* — Wenderoth, Lind & Ponack, L.L.P.

(57) ABSTRACT

The present invention provides an effective, selective, and industrially applicable process for producing 2,3,3,3-tetrafluoropropene. Specifically, the present invention provides a process for producing 2,3,3,3-tetrafluoropropene including reacting 2-chloro-3,3,3-trifluoropropene with hydrogen fluoride in the presence of oxygen and a catalyst comprising chromium oxide represented by the composition formula: $CrO_m$ ($1.5 < m < 3$), or fluorinated chromium oxide obtained by fluorinating the chromium oxide.

6 Claims, 1 Drawing Sheet

PROCESS FOR PREPARATION OF 2,3,3,3-TETRAFLUOROPROPENE

This application is a U.S. national stage of International Application No. PCT/JP2010/057727 filed Apr. 22, 2010, which claims the benefit of U.S. provisional application Ser. No. 61/202,967 filed Apr. 23, 2009.

TECHNICAL FIELD

The present invention relates to a process for producing 2,3,3,3-tetrafluoropropene.

BACKGROUND ART 2,3,3,3-Tetrafluoropropene, which is one of the halopropenes and represented by the chemical formula $CF_3CF=CH_2$ (HFC-1234yf), is a compound useful as a refrigerant, and is drawing attention as a constituent of a refrigerant or mixed refrigerant that can be used as an alternative for chlorofluorocarbon.

As one example of a method for producing HFC-1234yf, Patent Literature 1 discloses a method comprising reacting $CF_3CH=CHF$ (HFC-1234ze-E) in the presence of a Cr catalyst in a gas phase, thereby directly producing $CF_3CF=CH_2$ (HFC-1234yf). However, this method is in need of improvement because of low yield. Non-Patent Literature 1 discloses a method comprising reacting a compound represented by the chemical formula $CF_3CF_2CH_2X$ (X=Cl or I) with zinc (Zn) in ethanol, thereby producing HFC-1234yf in a single reaction step. However, this method is not suitable for industrial production because of the high cost of zinc, and the production of large amounts of waste.

Other examples of methods for producing HFC-1234yf include the following. Patent Literature 2 discloses a method comprising reacting chloromethyl tetrafluoropropanate with amine; Patent Literature 3 discloses a method comprising the thermal decomposition of 1-trifluoromethyl-1,2,2-trifluorocyclobutane; Patent Literature 4 discloses a method comprising reacting chlorotrifluoroethylene ($CClF=CF_2$) and methyl fluoride ($CH_3F$) in the presence of a Lewis acid such as $SbF_5$; and Patent Literature 5 discloses a method comprising the thermal decomposition of tetrafluoroethylene ($CF_2=CF_2$) and chloromethane ($CH_3Cl$). Non-Patent Literatures 2 and 3 listed below also disclose HFC-1234yf production methods.

However, such methods are not considered to be effective for industrial production since the starting materials are difficult to produce and are not easily obtained, the reaction conditions are severe, the reaction reagents are expensive, the yield is low, etc.

Further, Patent Literature 6 discloses a method comprising reacting 2-chloro-3,3,3-trifluoropropene represented by the chemical formula: $CF_3CCl=CH_2$ (HCFC-1233xf) with hydrogen fluoride in a gas phase under a pressurized condition, thereby producing HFC-1234yf. However, the selectivity of the target compound HFC-1234yf is about 40 to about 60%; therefore, this method is not considered a production method of HFC-1234yf with high selectivity.

Citation List

Patent Literature

PTL 1: US 2008/0058562 A1
PTL 2: Japanese Unexamined Patent Publication No. S63-211245
PTL 3: U.S. Pat. No. 3,996,299
PTL 4: US 2006/258891 A1
PTL 5: U.S. Pat. No. 2,931,840
PTL 6: WO2009/003084 A1

Non Patent Literatures

NPL 1: J. Chem. Soc., 1957, 2193-2197
NPL 2: J. Chem. Soc., 1970, 3, 414-421
NPL 3: J. Fluorine Chem., 1997, 82, 171-174

SUMMARY OF INVENTION

Technical Problem

The present invention was made in view of the problems of the prior art. A primary object of the present invention is to provide an industrially applicable process for effectively producing 2,3,3,3-tetrafluoropropene with high selectivity.

Solution to Problem

The present inventors conducted extensive research to achieve the above object. As a result, they found that 2,3,3,3-tetrafluoropropene can be prepared at a high selectivity, compared to conventional methods, by using as a starting material an easily available compound 2-chloro-3,3,3-trifluoropropene represented by the chemical formula $CF_3CCl=CH_2$ (HCFC-1233xf), and allowing the starting material to react with hydrogen fluoride in the presence of a specific catalyst and oxygen. Specifically, they found that 2,3,3,3-tetrafluoropropene can be prepared with extremely high selectivity by adjusting the reaction temperature, pressure, oxygen supply amount, and HF supply amount in a specific range, in the presence of a specific catalyst. Further, they found that 1,1,1,2,2-pentafluoropropane, which is the main by-product of the product obtained by this method, is effective as such, as an intermediate product that is exchangeable for various compounds, and that the target 2,3,3,3-tetrafluoropropene can be efficiently obtained by supplying 1,1,1,2,2-pentafluoropropane, which is isolated from the reaction product, to the starting material 2-chloro-3,3,3-trifluoropropene.

The present inventors conducted further research based on the above findings, and the present invention was thus accomplished. That is, the present invention provides the process for producing 2,3,3,3-tetrafluoropropene shown below.

1. A process for producing 2,3,3,3-tetrafluoropropene comprising reacting 2-chloro-3,3,3-trifluoropropene with hydrogen fluoride in the presence of oxygen and a catalyst comprising chromium oxide represented by a composition formula: CrOm (1.5<m<3), or fluorinated chromium oxide obtained by fluorinating the chromium oxide.

2. The process according to Item 1, wherein the reaction is conducted at a reaction temperature of 330 to 380° C., under a pressure of 0.08 to 0.2 MPa, using oxygen in an amount of 0.1 to 1 mol, and hydrogen fluoride in an amount of 4 to 30 mol, per mol of 2-chloro-3,3,3-trifluoropropene.

3. A process according to Item 1 or 2, further comprising the steps of:

separating a reaction mixture comprising 2,3,3,3-tetrafluoropropene into a component A comprising 2-chloro-3,3,3-trifluoropropene, a component B comprising 1,1,1,2,2-pentafluoropropane, and a component C comprising 2,3,3,3-tetrafluoropropene; and supplying the component(s) A and/or B to 2-chloro-3,3,3-trifluoropropene used as a starting material.

4. A process according to Item 1 or 2, further comprising the steps of:

separating a reaction mixture comprising 2,3,3,3-tetrafluoropropene into a component A comprising 2-chloro-3, 3,3-trifluoropropene, a component B comprising 1,1,1,2,2-pentafluoropropane, and a component C comprising 2,3,3,3-tetrafluoropropene, collecting the 1,1,1,2,2-pentafluoropropane from the component B, and supplying the component(s) A and/or C to 2-chloro-3,3,3-trifluoropropene used as a starting material.

The process for preparing 2,3,3,3-tetrafluoropropene according to the invention is described below in detail.

In the process of the present invention, 2-chloro-3,3,3-trifluoropropene, which is used as a starting material, is reacted with hydrogen fluoride (HF) in the presence of a specific catalyst and oxygen.

(1) Starting Material Compound

2-Chloro-3,3,3-trifluoropropene that is used as a starting material is a known compound easily obtained on an industrial scale. Such a compound is obtained by, for example, performing fluorination and dehydrochlorination in the presence of hydrogen fluoride, using $CCl_3CHClCH_2Cl$ (240ab) etc. as a starting material.

(2) Catalyst

In the present invention, usable as a catalyst is chromium oxide represented by the composition formula $CrOm$, wherein m is in the range of $1.5<m<3$, or fluorinated chromium oxide obtained by fluorinating the aforementioned chromium oxide.

Using such a specific catalyst, the 2-chloro-3,3,3-trifluoropropene is reacted with hydrogen fluoride (HF) in the presence of oxygen, thereby obtaining the target 2,3,3,3-tetrafluoropropene with high selectivity.

In the chromium oxide catalyst represented by the composition formula $CrOm$, m is in the range of $1.5<m<3$, preferably $1.8 \leq m \leq 2.5$, and more preferably $2.0 \leq m \leq 2.3$. An example of the preparation method of such chrome oxide is as follows:

First, an aqueous chromium salt solution (chromium nitrate, chromium chloride, chromium alum, chromium sulfate, or the like) and aqueous ammonia are mixed to obtain a precipitate of chromium hydroxide. For example, a precipitate of chromium hydroxide may be obtained by adding, to a 5.7% aqueous chromium nitrate solution, 10% aqueous ammonia dropwise in an amount of from 1 to about 1.2 equivalents of ammonia per equivalent of chromium nitrate. The properties of chromium hydroxide may be controlled by the reaction rate during the precipitation. The reaction rate is preferably fast; and the faster the reaction rate, the better the catalytic activity. The reaction rate varies depending on the temperature of the reaction solution, mixing procedure (mixing speed) of the aqueous ammonia, stirring conditions, etc. Accordingly, by adjusting these conditions, the reaction rate is controlled.

The obtained precipitate is filtrated, washed, and then dried. The drying may be carried out, for example, in air, at about 70 to about 200° C., particularly at about 120° C., for about 1 to about 100 hours, particularly about 12 hours. The product at this stage is referred to as in a chromium hydroxide state. Subsequently, the product is disintegrated into a powder. The rate of the precipitation is adjusted so that the disintegrated powder (for example, having a particle diameter of 1,000 μm or less, and 95% of the disintegrated powder having a particle diameter of from 46 to 1,000 μm) has a density of about 0.6 to about 1.1 g/ml, preferably about 0.6 to about 1.0 g/ml. A powder density of less than 0.6 g/ml is not preferable, since the pellet strength will be insufficient. Conversely, a powder density of more than 1.1 g/ml is also not preferable, since the catalyst activity will be degraded, and the pellets will break easily. The specific surface area of the powder is preferably about 100 $m^2/g$ or more, and more preferably about 120 $m^2/g$ or more, under degassing conditions at 200° C. for 80 minutes. The specific surface area used herein is referred to as a value measured by the BET method.

The obtained chromium hydroxide powder is formed into pellets by means of a tableting machine. If necessary, the chromium hydroxide powder may be mixed with graphite in an amount of about 3 wt. % or less. The pellets may have a diameter of, for example, about 3.0 mm, and a height of about 3.0 mm. The pellets preferably have a compressive strength (pellet strength) of about 210±40 kg/$cm^2$. An overly high compressive strength lowers the contact efficiency of the gas to decrease the catalytic activity, and makes the pellets easily breakable. Conversely, an overly low compressive strength causes the pellets to be easily pulverized, making handling difficult.

The formed pellets are calcined in an inert atmosphere, e.g., in a nitrogen stream, to yield an amorphous chromium oxide. The calcination temperature is preferably 360° C. or more. When the temperature is overly high, the pellets will be crystallized. For this reason, the temperature is preferably as high as possible within a range that can prevent crystallization. For example, the calcination may be performed at about 380 to about 460° C., preferably at about 400° C., for about 1 to about 5 hours, preferably for about 2 hours.

The specific surface area of the calcined chromium oxide may be about 170 $m^2/g$ or more, preferably about 180 $m^2/g$ or more, and more preferably about 200 $m^2/g$ or more. The upper limit of the specific surface area may be about 240 $m^2/g$, and more preferably about 220 $m^2/g$. A specific surface area of more than 240 $m^2/g$ results in an increased deterioration rate, in spite of the enhanced catalytic activity. Conversely, a specific surface area of less than 170 $m^2/g$ results in decreased catalytic activity, and is thus not preferable.

A fluorinated chromium oxide may be prepared according to the method disclosed in Japanese Unexamined Patent Publication No. H5-146680. For example, the chromium oxide obtained by the above method is fluorinated with hydrogen fluoride (HF treatment) to thereby obtain a fluorinated chromium oxide. The fluorination temperature may be adjusted so that the water to be generated is not condensed (for example, about 150° C. at 0.1 MPa). The upper limit of the temperature may be adjusted to a value where the catalyst does not undergo crystallization due to the heat of reaction. The pressure during the fluorination is not limited, but is preferably the same as the pressure for the catalytic reaction. The fluorination temperature may be, for example, about 100 to about 460° C.

The surface area of the catalyst is reduced by fluorination treatment. Generally, a greater specific surface area leads to higher catalytic activity. The specific surface area after fluorination may preferably be about 25 to about 130 $m^2/g$, and more preferably about 40 to about 100 $m^2/g$, but is not limited to this range.

The fluorination reaction of the chromium oxide may be carried out by supplying hydrogen fluoride to a reactor containing chromium oxide, prior to the reaction for producing 2,3,3,3-tetrafluoropropene. After the chromium oxide is fluorinated as above, the starting material is supplied to the reactor, thereby advancing the reaction for producing 2,3,3,3-tetrafluoropropene.

The fluorination may be performed to any extent, but the fluorine content is preferably about 10 to about 30 wt. %.

The chromium catalysts disclosed in Japanese Unexamined Patent Publication No. H11-171806 may also be used as a chromium oxide catalyst or fluorinated chromium oxide catalyst. Specifically, the chromium catalysts, which are in an amorphous state, comprise a chromium compound as a main component, to which at least one metal element selected from the group consisting of indium, gallium, cobalt, nickel, zinc and aluminum is added, wherein the average valence of the chromium in the chromium compound is +3.5 or more and +5.0 or less.

The catalyst comprising the chromium oxide or fluorinated chromium oxide mentioned above may be supported on a carrier such as alumina, activated carbon, and the like.

(3) Process for preparing 2,3,3,3-tetrafluoropropene

In the process of the present invention, the 2-chloro-3,3,3-trifluoropropene that is used as a starting material is reacted with hydrogen fluoride (HF) in the presence of oxygen and a catalyst comprising the chromium oxide or fluorinated chromium oxide.

The specific embodiment of the treatment process is not particularly limited. For example, a catalyst is placed into a tubular flow reactor, and then a starting material 2-chloro-3,3,3-trifluoropropene and hydrogen fluoride are introduced into the reactor together with oxygen to be reacted in a gas phase. Examples of the flow reactors include adiabatic reactors, multitubular reactors cooled using a heat transmitting medium, and the like. The reactors usable herein are preferably made of a material resistant to the corrosive action of hydrogen fluoride, such as Hastelloy, Inconel, Monel, or the like The starting material mentioned above may be supplied to the reactor as is, or after being diluted with an inert gas, such as nitrogen, helium, argon, or the like.

The reaction conditions are not particularly limited; however, the reaction temperature is generally in the range of about 50 to about 500° C., preferably about 150 to about 450° C., and more preferably about 200 to about 380° C. When the reaction temperature is higher than the above range, the amount of unfavorable by-product is increased; whereas when the reaction temperature is lower than the above range, the conversion rate of the starting material is decreased. A reaction temperature outside the above range is thus not preferable.

The oxygen supply amount may be set to about 0.05 to about 1 mol per mol of 2-chloro-3,3,3-trifluoropropene. When the amount of oxygen is low, the improvement effect in selectivity is low, whereas when the amount of oxygen is overly high, the oxygen is reacted with hydrogen chloride to generate water and chlorine, which advances unfavorable side reactions due to the generated chlorine. An oxygen supply amount outside the above range is thus not preferable.

The supply amount of hydrogen fluoride may be generally set to about 1.5 to about 100 mol per mol of 2-chloro-3,3,3-trifluoropropene.

To enhance the selectivity of the target 2,3,3,3-tetrafluoropropene, it is preferable to supply oxygen in an amount of about 0.1 to about 0.8 mol, and hydrogen fluoride in an amount of about 4 to about 30 mol per mol of 2-chloro-3,3,3-trifluoropropene; and it is more preferable to supply oxygen in an amount of about 0.15 to about 0.7 mol, and hydrogen fluoride in an amount of about 6 to about 20 mol per mol of 2-chloro-3,3,3-trifluoropropene.

The reaction temperature is preferably in the range of about 300° C. to about 380° C., and more preferably in the range of about 330° C. to about 380° C. The pressure during the reaction is preferably about 0.05 to about 0.2 MPa; a pressure at around atmospheric pressure is more preferable.

By using the specific chromium oxide, or the fluorinated chromium oxide as a catalyst, and by adjusting the oxygen supply amount, hydrogen fluoride supply amount, reaction temperature, and pressure in the above-mentioned range, the target 2,3,3,3-tetrafluoropropene can be obtained with particularly high selectivity, e.g., a selectivity of about 65% or more.

The reaction time is not particularly limited, but the contact time, which is represented by W/Fo, is generally about 0.1 to about 100 g·sec/cc, and preferably about 1.0 to about 50 g·sec/cc. W/Fo represents a ratio of a catalyst filling amount W (g) to the total flow rate (Fo) (flow rate at 0° C., 0.1 MPa: cc/sec) of starting material gas flowing to a reaction system. The total flow rate (Fo) refers to the flow rate of 2-chloro-3,3,3-trifluoropropene, hydrogen fluoride, and oxygen.

(4) Reaction Mixture

According to the above method, the target 2,3,3,3-tetrafluoropropene can be obtained at a high selectivity, i.e., a selectivity exceeding 65%, by suitably adjusting the reaction conditions.

The target 2,3,3,3-tetrafluoropropene can be isolated from the reaction mixture using known isolation means, such as distillation, liquid separation, extraction, extractive distillation, etc. The resulting 2,3,3,3-tetrafluoropropene can be effectively used as a constituent of a refrigerant or mixed refrigerant that can be used as an alternative for chlorofluorocarbon.

(5) Process of Circulation

The product obtained by the process of the present invention includes the target 2,3,3,3-tetrafluoropropene and the main by-product 1,1,1,2,2-pentafluoropropane represented by the chemical formula: $CF_3CF_2CH_2$ (HFC-245cb). In addition to the above, the product also includes 1,3,3,3-tetrafluoropropene (HFC-1234ze-E+Z), 1-chloro-3,3,3-trifluoropropene (HCFC-1233zd-E+Z), 1,1,1,3,3-pentafluoropropane (HFC-245fa), etc. Of these, the main by-product 1,1,1,2,2-pentafluoropropane itself is a useful compound as an intermediate product that is convertible for various compounds. Additionally, by supplying 1,1,1,2,2-pentafluoropropane that is isolated from the reaction mixture to the starting material 2-chloro-3,3,3-trifluoropropene, the entire reaction yield can be enhanced.

There is no limitation on the method for supplying 1,1,1,2,2-pentafluoropropane. For example, 1,1,1,2,2-pentafluoropropane may be supplied by the following method.

First, the product obtained by the process of the present invention is separated into a component A containing the starting material 2-chloro-3,3,3-trifluoropropene, a component B containing 1,1,1,2,2-pentafluoropropane, and a component C containing 2,3,3,3-tetrafluoropropene.

The separation method is not particularly limited, and can be suitably selected from, for example, distillation, liquid separation, extraction, extractive distillation, etc.

In particular, when separation is conducted by distillation, the component A containing the starting material 2-chloro-3,3,3-trifluoropropene (HCFC-1233xf) (boiling point: 14° C.), 1-chloro-3,3,3-trifluoropropene (HCFC-1233zd-E+Z) (boiling point of E-isomer: 17° C., Z-isomer: 35° C.), 1,1,1,3,3-pentafluoropropane (HFC-245fa) (boiling point: 15° C.) and 1,3,3,3-tetrafluoropropene (HFC-1234ze-Z) (boiling point of Z-isomer: 9° C.) is collected from the bottom of the distillation column; the component B containing 1,3,3,3-tetrafluoropropene (HFC-1234ze-E) (boiling point of E-isomer: −19° C.) and 1,1,1,2,2-pentafluoropropane (HFC-245cb) (boiling point: −18° C.) is collected from the middle of the distillation column; and the component C containing 2,3,3,3-tetrafluoropropene (HFC-1234yf) (boiling point: −28.3° C.) is collected from the top of the distillation column. Because hydrogen fluoride (boiling point: 19.4° C.) forms an azeotrope with 2,3,3,3-tetrafluoropropene, hydrogen fluoride is contained in both the component at the top of the column and the component at the bottom of the column. The hydrogen fluoride may be removed by washing with water or the like prior to the aforementioned separation treatment.

The components each obtained as above are, for example, treated according to the flow chart of FIG. 1, thereby collecting the target product 2,3,3,3-tetrafluoropropene. According to the flow chart of FIG. 1, the component C in the top of the distillation column 1 is transferred to the distillation column 2 to undergo distillation, allowing the target product 2,3,3,3-tetrafluoropropene to be collected from the top of the distillation column. The component B in the middle of the distillation column is transferred to a fluorination reactor, allowing the by-product 1,1,1,2,2-pentafluoropropane to be supplied to the starting material for effective use. The component A in the bottom of the distillation column is also transferred to the fluorination reactor to be supplied to the starting material, allowing the unreacted starting material 2-chloro-3,3,3-trifluoropropene in the component A to be used effectively.

According to the flow chart of FIG. 2, 1,1,1,2,2-pentafluoropropane (HFC-245cb) can be isolated and effectively used. Therefore, the process of the present invention is also applicable to the production of 1,1,1,2,2-pentafluoropropane. According to the flow chart of FIG. 2, the component B in the middle of the distillation column 1 is transferred to the distillation column 2 to undergo distillation, allowing 1,1,1,2,2-pentafluoropropane (HFC-245cb) to be collected from the bottom of the distillation column. The component A in the bottom of the distillation column 1 and the component C in the top of the distillation column 1 can be effectively used by supplying them to the fluorination reactor.

When 1,1,1,2,2-pentafluoropropane is isolated in accordance with the flow chart of FIG. 2, it is preferable to set the supply amount of hydrogen fluoride to about 4 to about 20 mol per mol of 2-chloro-3,3,3-trifluoropropene, and the reaction temperature to about 200° C. to about 330° C., in the production process of the present invention. By employing such reaction conditions, the selectivity of 1,1,1,2,2-pentafluoropropane is increased, thus ensuring the effective production of 1,1,1,2,2-pentafluoropropane.

ADVANTAGEOUS EFFECTS OF INVENTION

The process of the present invention ensures the effective and selective production of 2,3,3,3-tetrafluoropropene.

DESCRIPTION OF EMBODIMENTS

Figure 1:
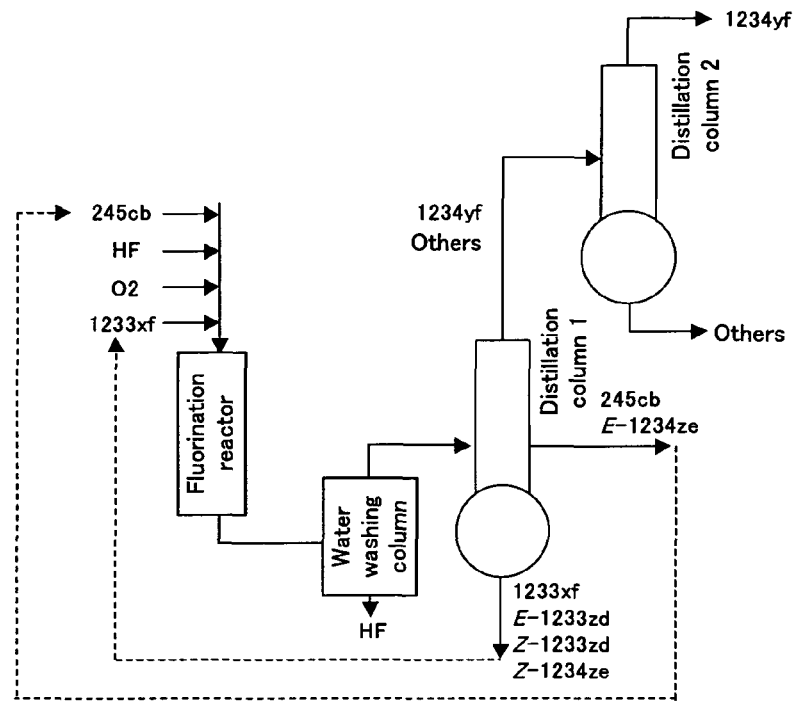
FIG. 1 is a flow chart showing an embodiment of the production process of the present invention.
Figure 2:
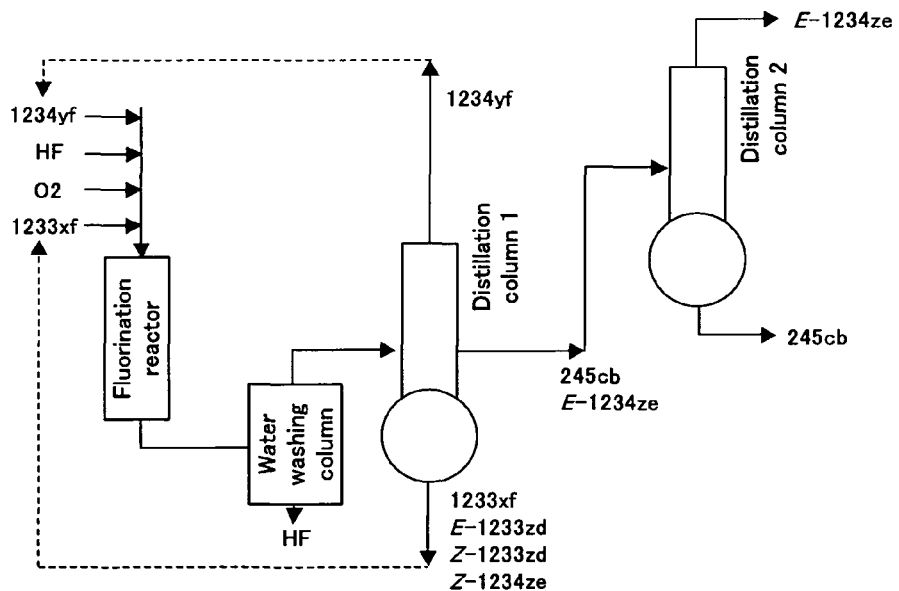
FIG. 2 is a flow chart showing another embodiment of the production process of the present invention.

Hereinbelow, the present invention is described in detail with reference to examples.

EXAMPLE 1

Production of 2,3,3,3-tetrafluoropropene

A 13.7 g amount of catalyst (fluorine content: about 15.0 wt. %) obtained by subjecting a chromium oxide represented by the composition formula $CrO_{2.0}$ to fluorination treatment was placed into a tubular Hastelloy reactor having an inside diameter of 15 mm and a length of 1 m. While the reactor was maintained at atmospheric pressure (0.1 MPa) at 360° C., 76 cc/min of anhydrous hydrogen fluoride (HF) (flow rate at 0° C., 0.1 MPa) was supplied to the reactor for 1 hour, and then 2.4 cc/min of oxygen (flow rate at 0° C., 0.1 MPa) was supplied to the reactor for 0.5 hours. Thereafter, while continuing the supply of HF and oxygen, 2-chloro-3,3,3-trifluoropropene was supplied at a rate of 4.7 cc/min (flow rate at 0° C., 0.1 MPa), and the reactor temperature was changed to 365° C.; thereby a reaction was initiated. The molar ratio of HF to 2-chloro-3,3,3-trifluoropropene was 16, the oxygen amount was 50 mol % relative to 2-chloro-3,3,3-trifluoropropene, and the contact time ($W/F_0$) was 10 g·sec/cc. 45 hours later, the outflow from the reactor was analyzed using gas chromatography. Table 1 shows the results.

The structures of the resulting products were as follows.
$CF_3CF=CH_2$ (HFC-1234yf)
$CF_3CF_2CH_3$ (HFC-245cb)
$CF_3CH=CH_2$ (HFC-1243zf)
$CF_3CH=CHF$ (HFC-1234ze-E)
$CF_3CH=CHF$ (HFC-1234ze-Z)
$CF_3CH=CHCl$ (HCFC-1233zd-E)
$CF_3CH=CHCl$ (HCFC-1233zd-Z)
$CF_3CCl=CHCl$ (HCFC-1223xd)
$CF_3CH_2CHF_2$ (HFC-245fa)

EXAMPLE 2

The same process was carried out in the same manner as in Example 1, except that the flow rate of the oxygen was changed to 0.9 cc/min. The molar ratio of HF to 2-chloro-3,3,3-trifluoropropene was 16, the oxygen amount was 20 mol % relative to 2-chloro-3,3,3-trifluoropropene, and the contact time (W/F0) was 10 g·sec/cc. 29 hours later, the outflow from the reactor was analyzed using gas chromatography. Table 1 shows the results of the analysis.

EXAMPLE 3

An 8.4 g amount of catalyst (fluorine content: about 15.0 wt. %) obtained by subjecting a chromium oxide represented by the composition formula $CrO_{2.0}$ to fluorination treatment was placed into a tubular Hastelloy reactor having an inside diameter of 15 mm and a length of 1 m. While the reactor was maintained at atmospheric pressure (0.1 MPa) at 345° C., 76 cc/min of anhydrous hydrogen fluoride (HF) (flow rate at 0° C., 0.1 MPa) was supplied to the reactor for 1 hour, and then 1.9 cc/min of oxygen (flow rate at 0° C., 0.1 MPa) was supplied to the reactor for 0.5 hours. Thereafter, while continuing the supply of HF and oxygen, 2-chloro-3,3,3-trifluoropropene was supplied at a rate of 9.6 cc/min (flow rate at 0° C., 0.1 MPa), and the reactor temperature was changed to 350° C.; thereby a reaction was initiated. The molar ratio of HF to 2-chloro-3,3,3-trifluoropropene was 8, the oxygen amount was 20 mol % relative to 2-chloro-3,3,3-trifluoropropene, and the contact time ($W/F_0$) was 5.8 g·sec/cc. 45 hours later, the outflow from the reactor was analyzed using gas chromatography. Table 1 shows the results of the analysis.

EXAMPLE 4

A 27.6 g amount of catalyst (fluorine content: about 15.0 wt. %) obtained by subjecting a chromium oxide represented by the composition formula $CrO_{2.0}$ to fluorination treatment was placed into a tubular Hastelloy reactor having an inside diameter of 15 mm and a length of 1 m. While the reactor was maintained at atmospheric pressure (0.1 MPa) at 370° C., 154 cc/min of anhydrous hydrogen fluoride (HF) (flow rate at 0° C., 0.1 MPa) was supplied to the reactor for 1 hour, and then 1.9 cc/min of oxygen (flow rate at 0° C., 0.1 MPa) was supplied to the reactor for 0.5 hours. Thereafter, while continuing the supply of HF and oxygen, 2-chloro-3,3,3-trifluoropropene was supplied at a rate of 11.6 cc/min (flow rate at 0° C., 0.1 MPa), and the reactor temperature was changed to 380° C.; thereby a reaction was initiated. The molar ratio of HF to 2-chloro-3,3,3-trifluoropropene was 13, the oxygen amount was 16 mol % relative to 2-chloro-3,3,3-trifluoropropene, and the contact time (W/F$_0$) was 10 g·sec/cc. 22 hours later, the outflow from the reactor was analyzed using gas chromatography. Table 1 shows the results of the analysis.

COMPARATIVE EXAMPLE 1

A 16.8 g amount of catalyst (fluorine content: about 15.0 wt. %) obtained by subjecting a chromium oxide represented by the composition formula $CrO_{0.2}$ to fluorination treatment was placed into a tubular Hastelloy reactor having an inside diameter of 15 mm and a length of 1 m. While the reactor was maintained at atmospheric pressure (0.1 MPa) at 340° C., 40 cc/min of anhydrous hydrogen fluoride (HF) (flow rate at 0° C., 0.1 MPa) was supplied to the reactor for 1 hour, and no oxygen was supplied. Thereafter, while continuing the supply of HF, 2-chloro-3,3,3-trifluoropropene was supplied at a rate of 12.0 cc/min (flow rate at 0° C., 0.1 MPa), and the reactor temperature was changed to 350° C.; thereby a reaction was initiated. The molar ratio of HF to 2-chloro-3,3,3-trifluoropropene was 3.3, and the contact time (W/F$_0$) was 19 g·sec/cc. 7 hours later, the outflow from the reactor was analyzed using gas chromatography. Table 1 shows the results of the analysis.

COMPARATIVE EXAMPLE 2

The same process was carried out in the same manner as in Comparative Example 1, except that the reaction temperature was changed to 300° C. 10 hours later, the outflow from the reactor was analyzed using gas chromatography. Table 1 shows the results of the analysis.

Table 1 shows that, according to Examples 1 to 4, HFC-1234yf was obtained with high selectivity, and the generation of unfavorable by-products was kept low. Table 1 also reveals that, according to Comparative Examples 1 and 2, 1234yf was obtained at a low yield, and the amount of unfavorable by-products was high.

EXAMPLE 5

A 19.1 g amount of catalyst (fluorine content: about 15.0 wt. %) obtained by subjecting a chromium oxide represented by the composition formula $CrO_{2.0}$ to fluorination treatment was placed into a tubular Hastelloy reactor having an inside diameter of 15 mm and a length of 1 m. While the reactor was maintained at atmospheric pressure (0.1 MPa) at 290° C., 46 cc/min of anhydrous hydrogen fluoride (HF) (flow rate at 0° C., 0.1 MPa) was supplied to the reactor for 1 hour, and then 1.9 cc/min of oxygen (flow rate at 0° C., 0.1 MPa) was supplied to the reactor for 0.5 hours. Thereafter, while continuing the supply of HF and oxygen, 2-chloro-3,3,3-trifluoropropene was supplied at a rate of 11.6 cc/min (flow rate at 0° C., 0.1 MPa), and the reactor temperature was changed to 300° C.; thereby a reaction was initiated. The molar ratio of HF to 2-chloro-3,3,3-trifluoropropene was 4, the oxygen amount was 16 mol % relative to 2-chloro-3,3,3-trifluoropropene, and the contact time (W/F$_0$) was 19 g·sec/cc. 4 hours later, the outflow from the reactor was analyzed using gas chromatography. Table 2 shows the results of the analysis.

EXAMPLE 6

A 33.1 g amount of catalyst (fluorine content: about 15.0 wt. %) obtained by subjecting a chromium oxide represented by the composition formula $CrO_{2.0}$ to fluorination treatment was placed into a tubular Hastelloy reactor having an inside diameter of 20 mm and a length of 1 m. While the reactor was maintained at atmospheric pressure (0.1 MPa) at 240° C., 80 cc/min of anhydrous hydrogen fluoride (HF) (flow rate at 0° C., 0.1 MPa) was supplied to the reactor for 1 hour, and then 1.9 cc/min of oxygen (flow rate at 0° C., 0.1 MPa) and 238 cc/min of nitrogen (flow rate at 0° C., 0.1 MPa) were supplied to the reactor for 0.5 hours. Thereafter, while continuing the supply of HF, oxygen and nitrogen, 2-chloro-3,3,3-trifluoropropene was supplied at a rate of 12.0 cc/min (flow rate at 0° C., 0.1 MPa), and the reactor temperature was changed to 250° C.; thereby a reaction was initiated. The molar ratio of HF to 2-chloro-3,3,3-trifluoropropene was 7, the oxygen amount was 16 mol % relative to 2-chloro-3,3,3-trifluoropropene and the contact time (W/F$_0$) was 6 g·sec/cc. 21 hours later, the outflow from the reactor was analyzed using gas chromatography. Table 2 shows the results.

TABLE 1

|  | Example | | | | Comparative Example | |
|---|---|---|---|---|---|---|
|  | Ex. 1 | Ex. 2 | Ex. 3 | Ex. 4 | Comp. Ex. 5 | Comp. Ex. 6 |
| Reaction Temperature (° C.) | 365 | 365 | 350 | 380 | 350 | 300 |
| Reaction Time (hr) | 45 | 29 | 45 | 22 | 7 | 10 |
| HF molar ratio | 16 | 16 | 8 | 13 | 3 | 3 |
| W/F$_0$ (g · sec/cc) | 10 | 10 | 5.8 | 10 | 19 | 19 |
| Amount of O$_2$ (mol %) | 50 | 20 | 20 | 16 | 0 | 0 |
| CF$_3$CCl=CH$_2$ Conversion (%) | 37.8 | 24.9 | 6.2 | 40.8 | 3.5 | 1.4 |
| Product Selectivity (%) | | | | | | |
| HFC-1234yf | 75.2 | 76.7 | 79.3 | 68.7 | 61.4 | 48.4 |
| HFC-245cb | 15.3 | 15.6 | 12.4 | 13.7 | 12.9 | 17.7 |
| HFC-1243zf | 0.1 | 0.1 | 0.1 | 0.3 | 8.8 | 1.9 |
| HFC-1234ze-E | 1.9 | 1.8 | 3.1 | 5.6 | 1.8 | 0.7 |
| HFC-1234ze-Z | 1.4 | 1.3 | 0.7 | 1.5 | 1.1 | 0.0 |
| HCFC-1233zd-E | 1.5 | 1.0 | 0.5 | 3.4 | 1.4 | 0.0 |
| HCFC-1233zd-Z | 0.3 | 0.2 | 0.1 | 0.5 | 0.0 | 0.0 |
| HCFC-1223xd | 0.3 | 0.2 | 0.1 | 0.9 | 0.1 | 0.6 |
| HFC-245fa | 0.1 | 0.1 | 0.1 | 0.1 | 0.0 | 0.0 |
| Others | 3.9 | 3.0 | 3.6 | 5.3 | 12.5 | 30.7 |

TABLE 2

|  | Example | |
|---|---|---|
|  | Ex. 5 | Ex. 6 |
| Reaction Temperature (° C.) | 300 | 250 |
| Reaction Time (hr) | 4 | 21 |
| HF molar ratio | 4 | 7 |
| W/F$_0$ (g · sec/cc) | 19 | 6 |
| Amount of O$_2$ (mol %) | 16 | 16 |
| CF$_3$CCl=CH$_2$ Conversion (%) | 9.2 | 5.9 |
| Product Selectivity (%) | | |
| HFC-1234yf | 44.0 | 26.9 |
| HFC-245cb | 48.6 | 60.6 |
| HFC-1243zf | 0.1 | 0.0 |

TABLE 2-continued

| | Example | |
|---|---|---|
| | Ex. 5 | Ex. 6 |
| HFC-1234ze-E | 0.2 | 0.3 |
| HFC-1234ze-Z | 0.1 | 0.1 |
| HCFC-1233zd-E | 0.4 | 0.8 |
| HCFC-1233zd-Z | 0.1 | 0.2 |
| HCFC-1223xd | 0.1 | 0.7 |
| HFC-245fa | 0.0 | 0.1 |
| Others | 6.4 | 10.3 |

The invention claimed is:

1. A process for producing 2,3,3,3-tetrafluoropropene comprising reacting 2-chloro-3,3,3-trifluoropropene with hydrogen fluoride in the presence of oxygen and a catalyst comprising chromium oxide represented by a composition formula: $CrO_m$ ($1.5<m<3$), or fluorinated chromium oxide obtained by fluorinating the chromium oxide.

2. The process according to claim 1, wherein the reaction is conducted at a reaction temperature of 330 to 380° C., under a pressure of 0.08 to 0.2 MPa, using oxygen in an amount of 0.1 to 1 mol, and hydrogen fluoride in an amount of 4 to 30 mol, per mol of 2-chloro-3,3,3-trifluoropropene.

3. A process according to claim 1, further comprising the steps of: separating a reaction mixture comprising 2,3,3,3-tetrafluoropropene into a component A comprising 2-chloro-3,3,3-trifluoropropene, a component B comprising 1,1,1,2,2-pentafluoropropane, and a component C comprising 2,3,3,3-tetrafluoropropene; and supplying the component(s) A and/or B to 2-chloro-3,3,3-trifluoropropene used as a starting material.

4. A process according to claim 1, further comprising the steps of: separating a reaction mixture comprising 2,3,3,3-tetrafluoropropene into a component A comprising 2-chloro-3,3,3-trifluoropropene, a component B comprising 1,1,1,2,2-pentafluoropropane, and a component C comprising 2,3,3,3-tetrafluoropropene, collecting the 1,1,1,2,2-pentafluoropropane from the component B, and supplying the component(s) A and/or C to 2-chloro-3,3,3-trifluoropropene used as a starting material.

5. A process according to claim 2, further comprising the steps of: separating a reaction mixture comprising 2,3,3,3-tetrafluoropropene into a component A comprising 2-chloro-3,3,3-trifluoropropene, a component B comprising 1,1,1,2,2-pentafluoropropane, and a component C comprising 2,3,3,3-tetrafluoropropene; and supplying the component(s) A and/or B to 2-chloro-3,3,3-trifluoropropene used as a starting material.

6. A process according to claim 2, further comprising the steps of: separating a reaction mixture comprising 2,3,3,3-tetrafluoropropene into a component A comprising 2-chloro-3,3,3-trifluoropropene, a component B comprising 1,1,1,2,2-pentafluoropropane, and a component C comprising 2,3,3,3-tetrafluoropropene, collecting the 1,1,1,2,2-pentafluoropropane from the component B, and supplying the component(s) A and/or C to 2-chloro-3,3,3-trifluoropropene used as a starting material.

* * * * *